US011058786B2

(12) United States Patent  (10) Patent No.: US 11,058,786 B2
Hopkinson et al.  (45) Date of Patent: *Jul. 13, 2021

(54) MEDICAL DEVICE TRANSPORT CONTAINERS

(71) Applicant: Merit Medical Systems, Inc., South Jordan, UT (US)

(72) Inventors: Aaron Hopkinson, Herriman, UT (US); Doug Hales, South Jordan, UT (US); Daniel Hadley, Herriman, UT (US); Dylan Neyme, Salt Lake City, UT (US); John William Hall, North Salt Lake, UT (US); Jeremy Snow, South Jordan, UT (US); Tyler David Rees, Draper, UT (US); Abbe M. Smith, West Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/714,367

(22) Filed: Dec. 13, 2019

(65) Prior Publication Data

US 2020/0188546 A1  Jun. 18, 2020

Related U.S. Application Data

(63) Continuation of application No. 15/286,923, filed on Oct. 6, 2016, now Pat. No. 10,532,117.

(Continued)

(51) Int. Cl.
*A61L 2/18* (2006.01)
*A61B 50/00* (2016.01)
(Continued)

(52) U.S. Cl.
CPC ............... *A61L 2/18* (2013.01); *A61B 50/00* (2016.02); *A61B 50/31* (2016.02); *A61B 2050/314* (2016.02); *A61L 2202/24* (2013.01)

(58) Field of Classification Search
CPC ....... A61L 2/18; A61L 2202/24; A61B 50/00; A61B 50/31
See application file for complete search history.

(56) References Cited

U.S. PATENT DOCUMENTS 5,028,147 A   7/1991  Graham
5,394,982 A * 3/1995  Sawaya ............... B65D 5/6611
                                                  206/366

(Continued)

FOREIGN PATENT DOCUMENTS

WO    2015028825    3/2015

OTHER PUBLICATIONS

Office Action dated Apr. 4, 2019 for U.S. Appl. No. 15/286,923.

*Primary Examiner* — Sean E Conley
(74) *Attorney, Agent, or Firm* — Stoel Rives LLP

(57) ABSTRACT

Medical containers are provided, wherein the containers may be used to transport medical devices. The medical container can include a front panel, a rear panel, and a lower panel cooperating to form a cavity. The lower panel may include an absorbent material. The medical container may also include one or more absorbent band members disposed around at least a portion of the circumference of the cavity. An insert portion including a front panel, a rear panel, and a lower panel may be coupled to or disposed within the medical container. The insert portion may be formed from an absorbent material. Methods of using the medical containers are also provided.

12 Claims, 10 Drawing Sheets

Related U.S. Application Data

(60) Provisional application No. 62/363,598, filed on Jul. 18, 2016, provisional application No. 62/239,683, filed on Oct. 9, 2015.

(51) Int. Cl.
*A61B 50/31* (2016.01)
*A61B 50/30* (2016.01)

(56) References Cited

U.S. PATENT DOCUMENTS

| | | |
|---|---|---|
| 5,401,102 A | 3/1995 | Faltynek |
| 5,490,841 A * | 2/1996 | Landis ............... A61M 5/3216 604/110 |
| 5,839,572 A | 11/1998 | Yeager |
| 6,073,372 A | 6/2000 | Davis |
| 8,596,458 B1 | 12/2013 | Alcorn |
| 2003/0190097 A1 | 10/2003 | Hanjianpour |
| 2005/0173439 A1 | 8/2005 | Chen |
| 2005/0265636 A1 | 12/2005 | Michalsky |
| 2006/0233470 A1 | 10/2006 | Jacoby |
| 2006/0269725 A1 | 11/2006 | Fai |
| 2007/0084866 A1 | 4/2007 | Saeugling |
| 2009/0080811 A1 | 3/2009 | Stefanek |
| 2015/0291352 A1 | 10/2015 | Morgan |

* cited by examiner

MEDICAL DEVICE TRANSPORT CONTAINERS

TECHNICAL FIELD

This application is a continuation of U.S. patent application Ser. No. 15/286,923, filed on Oct. 6, 2016 and titled, "Medical Device Transport Containers", which claims priority to U.S. Provisional Application No. 62/239,683, filed on Oct. 9, 2015 and titled, "Medical Device Transport Containers," and U.S. Provisional Application No. 62/363,598, filed on Jul. 18, 2016 and titled, "Medical Device Transport Containers," all of which are hereby incorporated by reference in their entireties.

TECHNICAL FIELD

The present disclosure relates generally to medical containers such as bags, and more particularly to medical containers for use in transporting medical devices. Methods of using the medical containers to transport medical devices are also disclosed.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Figure 1:
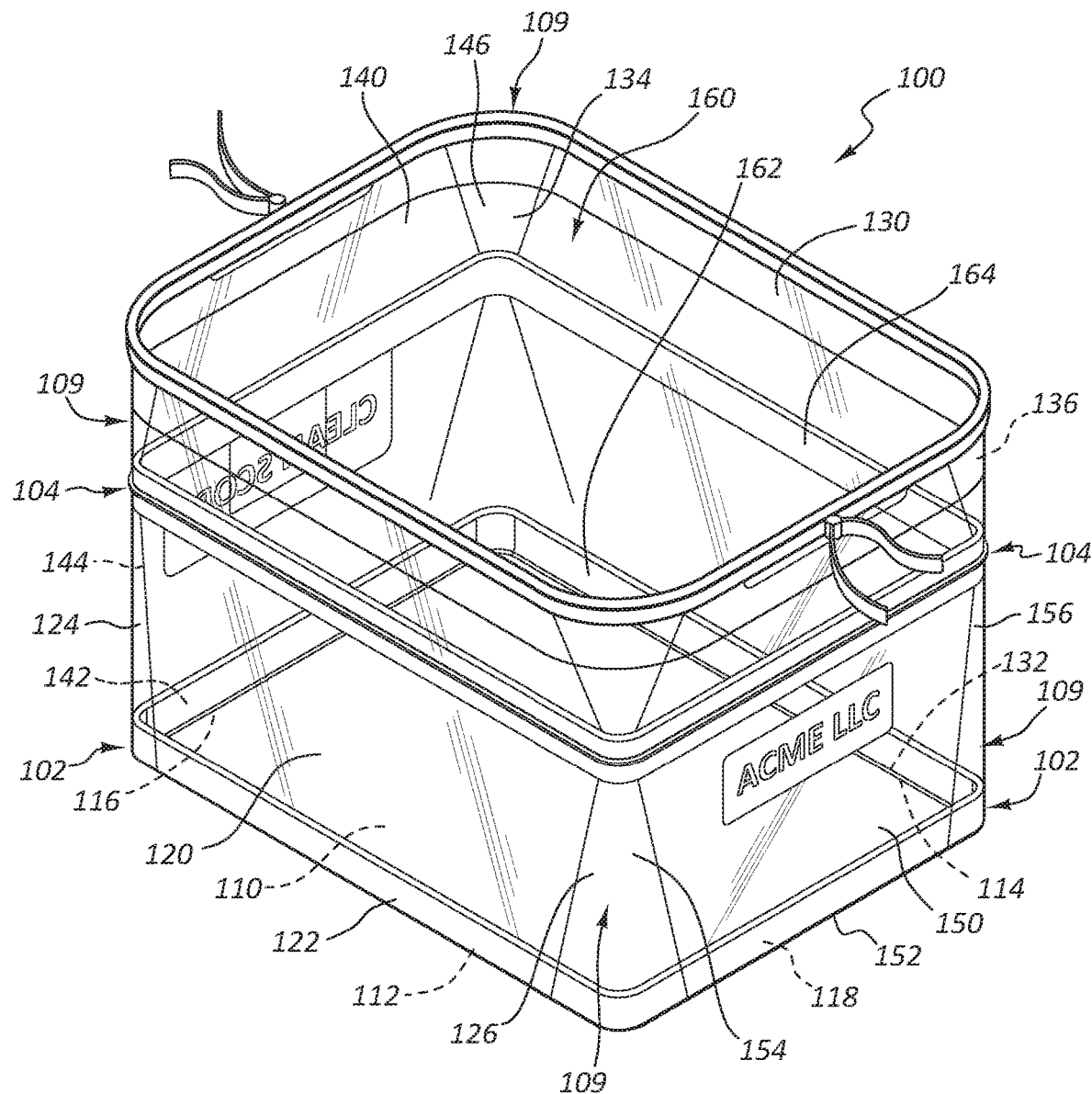
FIG. 1 is a perspective view of an embodiment of a medical device transport container.

A medical container or bag may be configured to transport a medical device. In some configurations, the container may include a front panel disposed opposite of a rear panel. The front panel and the rear panel may extend upwardly from a lower panel comprising an absorbent material. Each of the front panel, the rear panel, and the lower panel may cooperate to form at least a portion of a cavity.

Additionally, a first band member comprising an absorbent material may be disposed along at least a portion of a circumference of the cavity. The first band member may be configured to inhibit or prevent the flow of a fluid from within the cavity of the container to a position exterior of the container.

In some other configurations, an insert portion may be coupled to or disposed within the container. The insert portion may include a front panel, a rear panel, and a lower panel cooperating to form at least a portion of an insert cavity. Each of the front panel, the rear panel, and the lower panel may include an absorbent material.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. Components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

FIG. 1 illustrates an embodiment of a medical device transport container 100. The container 100 of the illustrated embodiment comprises a bag. In some other embodiments, the container 100 may comprise a box, a canister, a carton, a pouch, or another suitable holder for an object. The container 100, as depicted, comprises a first panel or front panel 120 disposed substantially opposite of a second panel or rear panel 130. Directional terms, such as "front," "rear," "lower," etc., are used herein with respect to the orientations shown in FIGS. 1-8B. The terms are used for the sake of convenience and are not necessarily intended to be limiting. Additionally, the container 100 comprises a first side panel 140 extending or disposed between each of the first panel 120 and the second panel 130. A second side panel 150 is disposed substantially opposite of the first side panel 140, and the second side panel 150 extends or is disposed between each of the first panel 120 and the second panel 130.

As illustrated, the container 100 can further comprise a lower panel 110. In some embodiments, the lower panel 110 comprises an absorbent material. In certain embodiments, the lower panel 110 can be coupled to an absorbent material. For example, an absorbent pad may be disposed adjacent the lower panel 110 and/or the absorbent pad may be coupled directly to the lower panel 110. The absorbent pad may form or provide the shape of a lower portion 102 of the container 100. As illustrated, the shape of the lower portion 102 and/or lower panel 110 of the container 100 is substantially rectangular. In some other embodiments, the shape of the lower portion 102 and/or the lower panel 110 of the container 100 may be substantially square, substantially circular, substantially oval, etc. Any other suitable shape can also be used. For example, the shape of the lower portion 102 and/or lower panel 110 of the container 100 can be non-rectangular and/or irregular (i.e., not a traditionally defined shape). Embodiments wherein the lower panel 110 does not comprise an absorbent material or wherein the lower panel 110 is not coupled to an absorbent material are also within the scope of the present disclosure.

The lower panel 110 can be coupled to a lower edge or lower panel edge 122, 132, 142, 152 of the first panel 120, the second panel 130, the first side panel 140, and/or the second side panel 150, respectively. In some embodiments, an absorbent edge or portion may be disposed at or adjacent the lower panel edge 122, 132, 142, 152 of the first panel 120, the second panel 130, the first side panel 140, and/or the second side panel 150, respectively. The absorbent edge may be configured to absorb one or more fluids. For example, a fluid may flow into or be disposed within a portion of a cavity 160 of the container 100 and the absorbent edge may be configured to absorb at least a portion of the fluid. In some embodiments, the absorbent edge may comprise a second band member 162 as detailed herein.

As depicted in FIG. 1, each of the lower panel 110, the first panel 120, the second panel 130, the first side panel 140, and the second side panel 150 can cooperate to form at least a portion of a cavity or void 160 within at least a portion of an interior of the container 100. In some embodiments, the container 100 may only comprise a subset of the panels (e.g., only a first panel 120 and a second panel 130), and the subset of panels may likewise cooperate to form the cavity 160.

Also within the scope of the present disclosure are containers comprising a single geometrically continuous wall or panel, for example, wherein a single panel is disposed in a continuous arc or curve, such as a bag comprising a continuous circular wall. The first panel, second panel, first side panel, second side panel, and/or lower panel, as described herein, may thus be understood as referring to portions of a single continuous wall or panel. In some embodiments, such portions may be integral and may not be divided or separated by seams, corners, or other components of the single geometrically continuous panel.

The cavity 160 may be configured to receive and retain a medical device, such as an endoscope. Other contents of the cavity 160 are also within the scope of this disclosure. In certain embodiments, the container 100 may be configured to protect a content of the container 100. For example, the container 100 may inhibit or prevent a medical device that is retained within the cavity 160 from being broken or damaged. The container 100 may also isolate a clean medical device such that the clean medical device is inhibited or prevented from becoming contaminated. Likewise, the container 100 may isolate a contaminated medical device such that the contaminated medical device is inhibited or prevented from contaminating objects that are exterior of the container 100.

In some embodiments, the container 100 may further comprise a first band member 164. The first band member 164 may comprise an absorbent material, and/or the first band member 164 may be coupled to an absorbent material. Embodiments wherein the first band member 164 does not comprise an absorbent material or wherein the first band member 164 is not coupled to an absorbent material are also within the scope of the present disclosure. As illustrated, the first band member 164 may be disposed along at least a portion of a circumference of the cavity 160. The first band member 164 may be coupled to or disposed along a middle portion 104 of each of the first panel 120, the second panel 130, the first side panel 140, and/or the second side panel 150. Analogously, in embodiments wherein the container 100 comprises only a subset of the panels or only a single panel, the first band member 164 may be coupled to or disposed along the middle portion 104 of the subset of panels or the single panel.

In various embodiments, the first band member 164 may be configured to inhibit or prevent fluid flow from within at least a portion of the cavity 160 of the container 100 to a position exterior of the container 100. For example, a fluid may be disposed or present in the lower portion 102 of the cavity 160. The container 100 may be tipped onto its side (i.e., on to one of the first panel 120, the second panel 130, the first side panel 140, or the second side panel 150) resulting in the flow of the fluid from within the cavity 160 of the container 100 toward a position exterior of the container 100. The first band member 164 may be configured to absorb at least a portion of the fluid such that the absorbed fluid does not flow out of the cavity 160 of the container 100.

The first band member 164 may tend to maintain its shape, including embodiments where it is substantially rigid or stiff. For example, the first band member 164 may be formed from a material that is more rigid than the materials from which one or more of the first panel 120, the second panel 130, the first side panel 140, and/or the second side panel 150 are formed. Likewise, in embodiments of the container 100 comprising only a single continuous panel or a subset of the panels 120, 130, 140, 150, the first band member 164 may be formed from a material that is more rigid than the materials from which the single continuous panel or the subset of panels are formed. Consequently, the first band member 164 may be configured to support or reinforce at least a portion of the container 100 (e.g., the middle portion 104). In another example, the container 100 may be thicker at the portion wherein each of the first panel 120, the second panel 130, the first side panel 140, and/or the second side panel 150 is coupled to the first band member 164. Such increased thickness may act to support or reinforce at least a portion of the container 100.

In certain embodiments, the container 100 may further comprise a second band member 162. The second band member 162 may comprise an absorbent material, and/or the second band member 162 may be coupled to an absorbent material. In various embodiments, the second band member 162 and/or the absorbent material of the second band member 162 may be coupled to the absorbent material of the lower panel 110. In some embodiments, the second band member 162 and/or the absorbent material of the second band member 162 may be integral with the lower panel 110 and/or the absorbent material of the lower panel 110. Embodiments wherein the second band member 162 does not comprise an absorbent material or wherein the second band member 162 is not coupled to an absorbent material are also within the scope of the present disclosure.

As illustrated, the second band member 162 may be disposed along at least a portion of the circumference of the cavity 160. Additionally, the second band member 162 may be coupled to or disposed along at least a portion of the lower portion 102 of each of the first panel 120, the second panel 130, the first side panel 140, and/or the second side panel 150. In some embodiments, the second band member 162 may create or form an absorbent basin or three-dimensional portion within the container 100 and/or the cavity 160.

In various embodiments, the second band member 162 may be configured to inhibit or prevent fluid flow from at least a portion of the cavity 160 of the container 100 to a position exterior of the container 100. As discussed above, a fluid may be disposed in a lower portion 102 of the cavity 160 of the container 100. The container 100 may be tipped onto its side resulting in the flow of the fluid from within the cavity 160 of the container 100 toward a position exterior of the container 100. The second band member 162 may be configured to absorb at least a portion of the fluid such that the absorbed fluid does not flow out of the cavity 160 of the container 100.

The second band member 162 may tend to maintain its shape, including embodiments where it is substantially rigid or stiff. For example, analogous to the first band member 164, the second band member 162 may be formed from a material that is more rigid than the materials from which one or more of the first panel 120, the second panel 130, the first side panel 140, and/or the second side panel 150 are formed. Likewise, in embodiments of the container 100 comprising only a single continuous panel or a subset of the panels 120, 130, 140, 150, the second band member 162 may be formed from a material that is more rigid than the materials from which the single continuous panel or the subset of panels are formed. Consequently, the second band member 162 may be configured to support or reinforce at least a portion of the container 100 (e.g., the lower portion 102). In another example, the container 100 may be thicker at the portion wherein the first panel 120, the second panel 130, the first side panel 140, and/or the second side panel 150 are coupled to the second band member 162. Such increased thickness may support or reinforce at least a portion of the container 100.

In some embodiments, the container 100 may comprise another number of band members, analogous to the first band member 164 and/or the second band member 162. For example, the container 100 may comprise one, two, three, four, five, or more band members. In certain embodiments, a third band member may be disposed between each of the first band member 164 and the second band member 162. In certain other embodiments, a fourth band member may be disposed above the first band member 164. Other configurations of the band members are also within the scope of this disclosure.

The first band member 164 and/or the second band member 162 may further comprise a stiffening member. For example, the first band member 164 and/or the second band member 162 may include a wire (e.g., a metal wire). The stiffening member may enhance or increase the rigidity or stiffness of the first band member 164 and/or the second band member 162 in comparison to a band member lacking such a stiffening member.

In various embodiments, the height of the first band member 164 may be about 0.1 inches to about 4 inches. In various other embodiments, the height of the first band member 164 may be about 0.5 inches to about 3.5 inches, about 1 inch to about 3 inches, about 1.5 inches to about 2.5 inches, or about 2 inches. Any other suitable height of the first band member 164 is also within the scope of this disclosure. Likewise, in certain embodiments, the height of the second band member 162 may be about 0.1 inches to about 4 inches. In certain other embodiments, the height of the second band member 162 may be about 0.5 inches to about 3.5 inches, about 1 inch to about 3 inches, about 1.5 inches to about 2.5 inches, or about 2 inches. Any other suitable height of the second band member 162 is also within the scope of this disclosure.

In some embodiments, one or more of the components of the container 100 may be integral. For example, each of the first panel 120 and the second side panel 150 may be formed from a single piece of material. In certain embodiments, each of the lower panel 110, the first panel 120, the second panel 130, the first side panel 140, and the second side panel 150 can be integral. In some other embodiments, one or more of the components of the container 100 may be independent or separate. For example, the first panel 120 may be formed from a first piece of material and the second side panel 150 may be formed from a second piece of material.

In some embodiments, the length of the container 100 may be about 8 inches to about 30 inches. In some other embodiments, the length of the container 100 may be about 10 inches to about 28 inches, about 12 inches to about 26 inches, about 14 inches to about 24 inches, about 16 inches to about 26 inches, or about 18 inches to about 20 inches. Any other suitable length of the container 100 is also within the scope of this disclosure. In some embodiments, the width of the container 100 may be about 8 inches to about 21 inches. In some other embodiments, the width of the container 100 may be about 10 inches to about 19 inches, about 12 inches to about 17 inches, or about 14 inches to about 15 inches. Any other suitable width of the container 100 is also within the scope of this disclosure. In some embodiments, the height of the container 100 may be about 6 inches to about 18 inches. In some other embodiments, the height of the container 100 may be about 8 inches to about 16 inches, about 10 inches to about 14 inches, or about 12 inches. Any other suitable height of the container 100 is also within the scope of this disclosure.

With continued reference to FIG. 1, the first panel 120 can comprise a lower panel edge 122 that may be coupled to a first panel edge 112 of the lower panel 110. The first panel 120 can further comprise a first side panel edge 124 disposed opposite of a second side panel edge 126. Analogous to the first panel 120, the second panel 130 can comprise a lower panel edge 132. The lower panel edge 132 can be coupled to a second panel edge 114 of the lower panel 110. The second panel 130 can further comprise a first side panel edge 134 disposed opposite of a second side panel edge 136. As discussed above, in some embodiments, the container 100 may be formed from a single geometrically continuous panel. In such configurations, the terms first panel, second panel, first side panel, second side panel, and/or lower panel may refer to portions of the single continuous panel, and the portions of such a single continuous panel may not be physically distinct, for example, the portions may not be separated by a seam, corner, or other component of the single continuous panel.

The first side panel 140, as illustrated, can comprise a first panel edge 144 that can be coupled to the first side panel edge 124 of the first panel 120. Analogously, a second panel edge 146 of the first side panel 140 can be coupled to the first side panel edge 134 of the second panel 130. Furthermore, the first side panel 140 can comprise a lower panel edge 142 that can be coupled to a first side panel edge 116 of the lower panel 110.

The second side panel 150 can comprise a first panel edge 154 that can be coupled to the second side panel edge 126 of the first panel 120. Furthermore, the second side panel 150 can comprise a second panel edge 156 that can be coupled to the second side panel edge 136 of the second panel 130. The second side panel 150 can also comprise a lower panel edge 152 that can be coupled to a second side panel edge 118 of the lower panel 110.

In certain embodiments, at least a portion of one or more of each of the first panel 120, the second panel 130, the first side panel 140, and/or the second side panel 150 may tend to hold a shape, including embodiments wherein it is substantially rigid, such that at least a portion of the container 100 is configured to stand substantially upright. In some embodiments, one or more support members (not shown) may be coupled to one or more portions of the container 100. For example, at least one elongate support member may be coupled at or adjacent at least a portion of at least one corner 109 of the container 100. In some embodiments, one or more support members may be coupled to at least one corner 109, at least two corners 109, at least three corners 109, at least four corners 109, etc. of the container 100. One or more support members may also be coupled to one or more other suitable portions of the container 100.

As discussed above, the container 100 may be configured to stand upright. In other words, the container 100 may be capable of standing on its own. The container 100 may also be substantially capable of maintaining its structural conformation. In certain embodiments, the lower panel 110 of the container 100 may serve as a base on which the container 100 rests. The first panel 120, the second panel 130, the first side panel 140, and/or the second side panel 150 may extend upwardly from the lower panel 110. The first panel 120, the second panel 130, the first side panel 140, and/or the second side panel 150 may also be attached or otherwise directly coupled to the lower panel 110. In other embodiments, one or more of the first panel 120, the second panel 130, the first side panel 140, and/or the second side panel 150 may be integrally formed with the lower panel 110. For example, each of the first panel 120, the second panel 130, the first side panel 140, and the second side panel 150 may be formed from a single piece of material.

As described above, the lower panel 110, the first panel 120, the second panel 130, the first side panel 140, and/or the second side panel 150 may be coupled at multiple positions. The lower panel 110, the first panel 120, the second panel 130, the first side panel 140, and/or the second side panel 150 may be coupled by a variety of mechanisms, for example, by a seam. The seam may comprise a seal, such as a heat seal. In some embodiments, the seam may be formed via an adhesive, stitching, or any other suitable method. The seam may or may not be airtight and/or liquid-tight.

Any variety of materials may be used to form the container 100. For example, in some instances, it may be desirable to select materials that are relatively stiff such that the container 100 is sufficiently rigid to hold or maintain its structure or conformation. It may also be desirous to form a container 100 that is relatively flexible. The container 100 may comprise a polymer, a fabric, or another suitable material. In some embodiments, the container 100 may be formed from polyethylene. In certain embodiments, the thickness of the polyethylene may be about 0.5 thousandth of an inch to about 5.5 mil thousandths of an inch. In certain other embodiments, the thickness of the polyethylene may be about 1 thousandth of an inch to about 5 thousandths of an inch, about 1.5 thousandths of an inch to about 4.5 thousandths of an inch, or about 2 thousandths of an inch to about 4 thousandths of an inch. Any other suitable thickness of polyethylene is also within the scope of this disclosure.

Figure 2:
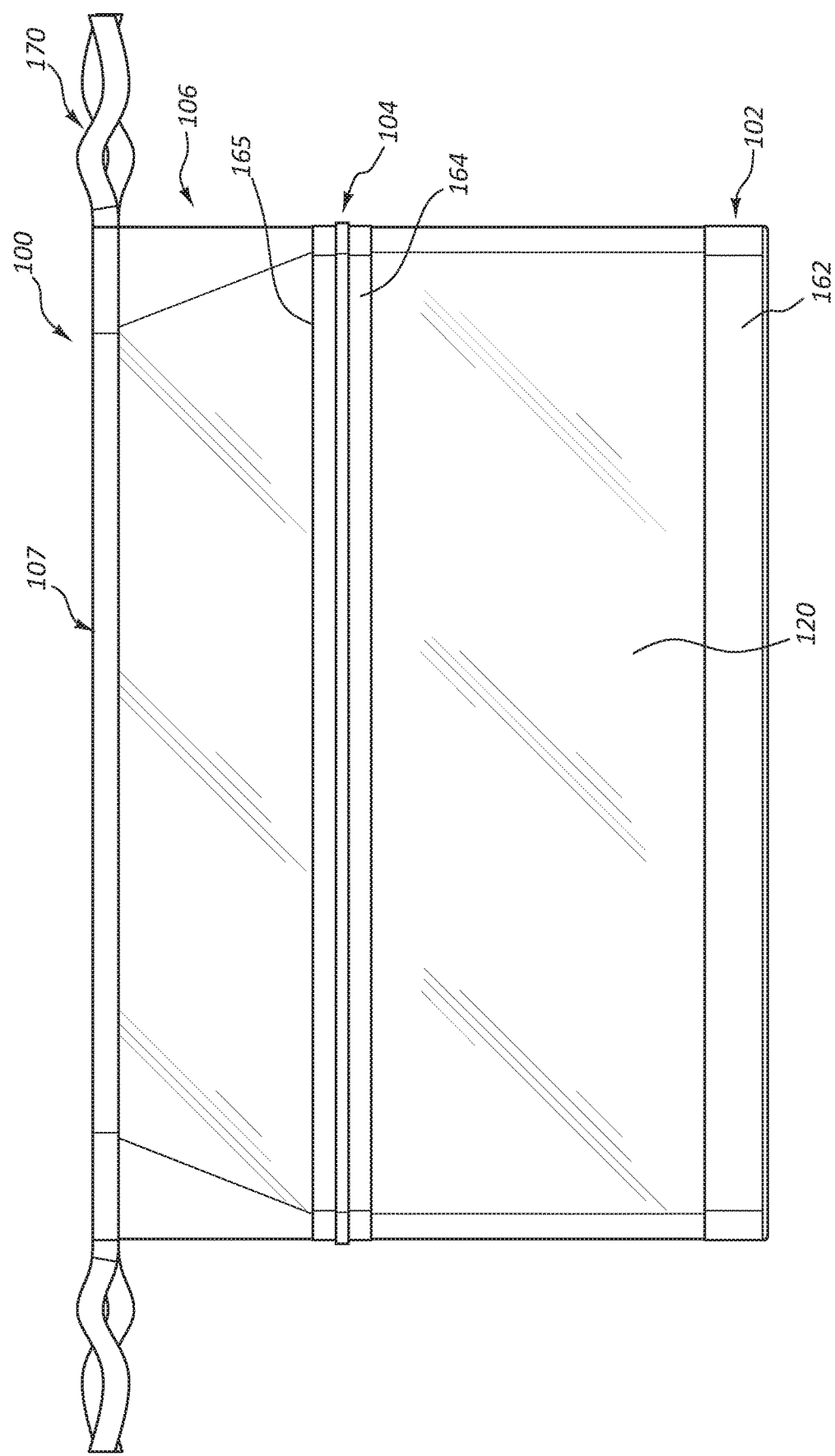
FIG. 2 is a side view of the medical device transport container of FIG. 1.

FIG. 2 is a side view of the container 100 of FIG. 1 showing the first panel 120. As illustrated, the container 100 can comprise the lower portion 102 disposed at or adjacent a base or bottom of the container 100. The container 100 can also comprise an upper portion 106 disposed at or adjacent the top of the container 100. Furthermore, the container 100 can comprise the middle portion 104 disposed between each of the lower portion 102 and the upper portion 106 of the container 100.

In various embodiments, the upper portion 106 may be defined as the portion of the container 100 disposed between each of an upper edge 165 of the first band member 164 and an upper edge 107 of the container 100. In some embodiments, the height of the upper portion 106 may be about 2 inches to about 10 inches. In some other embodiments, the height of the upper portion 106 may be about 3 inches to about 9 inches, about 4 inches to about 8 inches, about 5 inches to about 7 inches, about 4 inches, about 6 inches, or about 8 inches. Any other suitable height of the upper portion 106 is also within the scope of this disclosure.

As illustrated, the second band member 162 may be disposed at or adjacent the lower portion 102 of the container 100. Additionally, the first band member 164 may be disposed at or adjacent the middle portion 104 of the container 100.

In some embodiments, the upper portion 106 of the container 100 may be substantially flexible and each of the middle portion 104 and the lower portion 102 may be substantially rigid. For example, the upper portion 106 may be more flexible than each of the middle portion 104 and the lower portion 102. Other combinations of rigidity and/or flexibility of each of the lower portion 102, the middle portion 104, and/or the upper portion 106 (or other portions) of the container 100 are also within the scope of this disclosure. For example, the middle portion 104 may be substantially flexible and the lower portion 102 may be more rigid than each of the middle portion 104 and the upper portion 106 of the container 100.

With continued reference to FIG. 2, the container 100 may further comprise a closing member 170. The closing member 170 may be configured to transition the container 100 between each of an open configuration and a closed configuration. Furthermore, the closing member 170 may be configured to transition the container 100 from an open configuration, or a fully open configuration, as depicted in each of FIGS. 1 and 2, to a partially open configuration. The closing member 170 may be further configured to transition the container 100 from the partially open configuration to a partially closed configuration and from the partially closed configuration to the closed configuration, or a fully closed configuration. In some embodiments, the closing member 170 may comprise a drawstring, wherein the drawstring is disposed within at least a portion of the upper edge 107 or at least a portion of the upper portion 106 of the container 100. Other types of closing members 170 including, but not limited to, snaps, latches, zippers, hook and loop fasteners, buttons, hook and eye closures, and adhesives are also within the scope of this disclosure.

Figure 3:
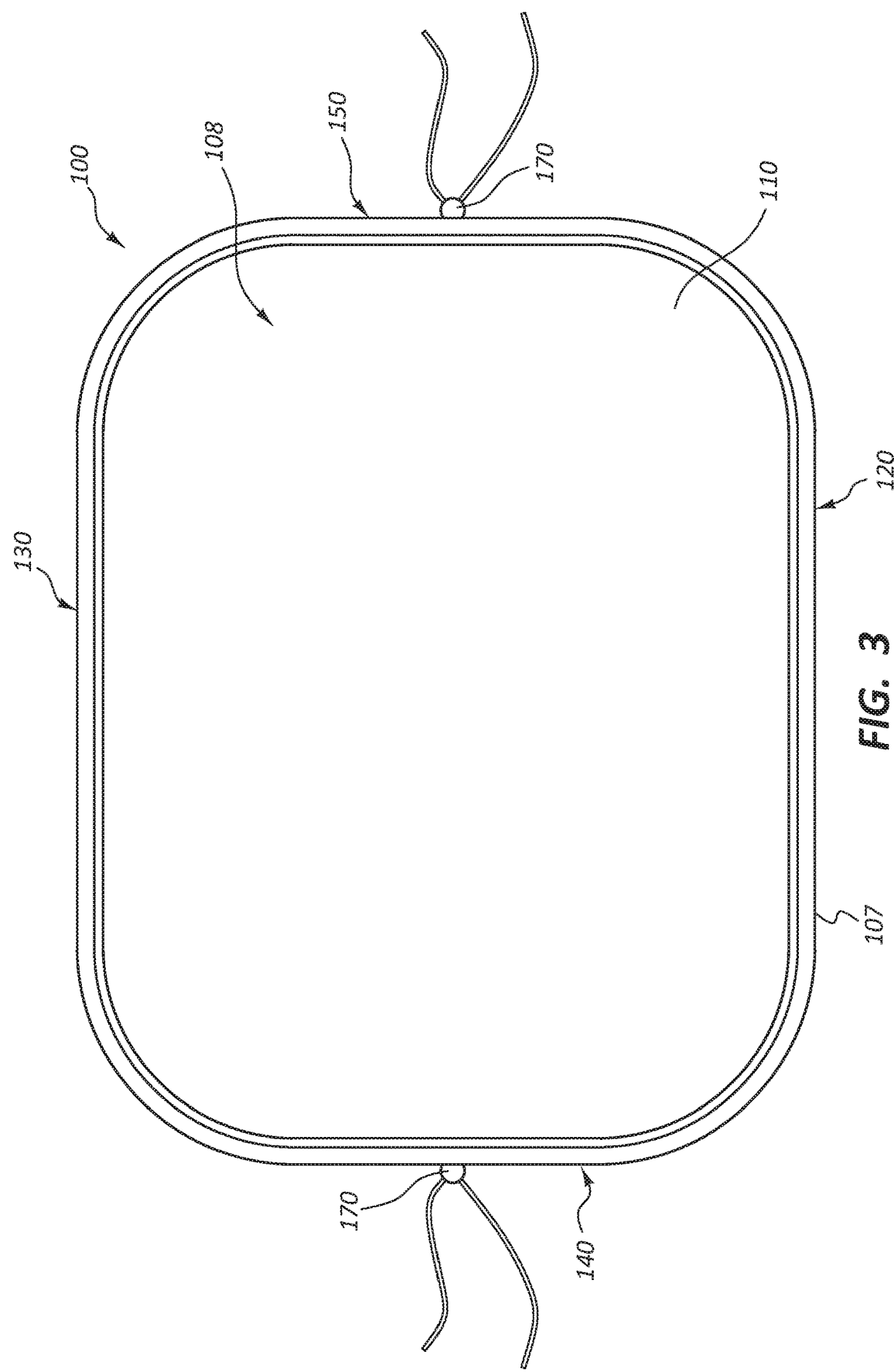
FIG. 3 is a top view of the medical device transport container of FIG. 1.

FIG. 3 is a top view of the container 100 of FIG. 1. As illustrated, the container 100 can comprise an opening 108. The upper edge 107 of the container 100 may define a circumference of the opening 108. In some embodiments, the upper edge 107 of each of the first panel 120, the second panel 130, the first side panel 140, and/or the second side panel 150 may cooperate to form the opening 108. In certain embodiments, the first band member 164, the second band member 162, the first panel 120, the second panel 130, the first side panel 140, and/or the second side panel 150 may tend to support or hold open the shape of the container 100. As discussed above, the closing member 170 may be disposed within or adjacent at least a portion of the upper edge 107 of the container 100. In some embodiments, the closing member 170 may extend around at least a portion of the circumference of the opening 108. Furthermore, the lower panel 110 can be disposed at a lower edge of each of the first panel 120, the second panel 130, the first side panel 140, and/or the second side panel 150.

Figure 4A:
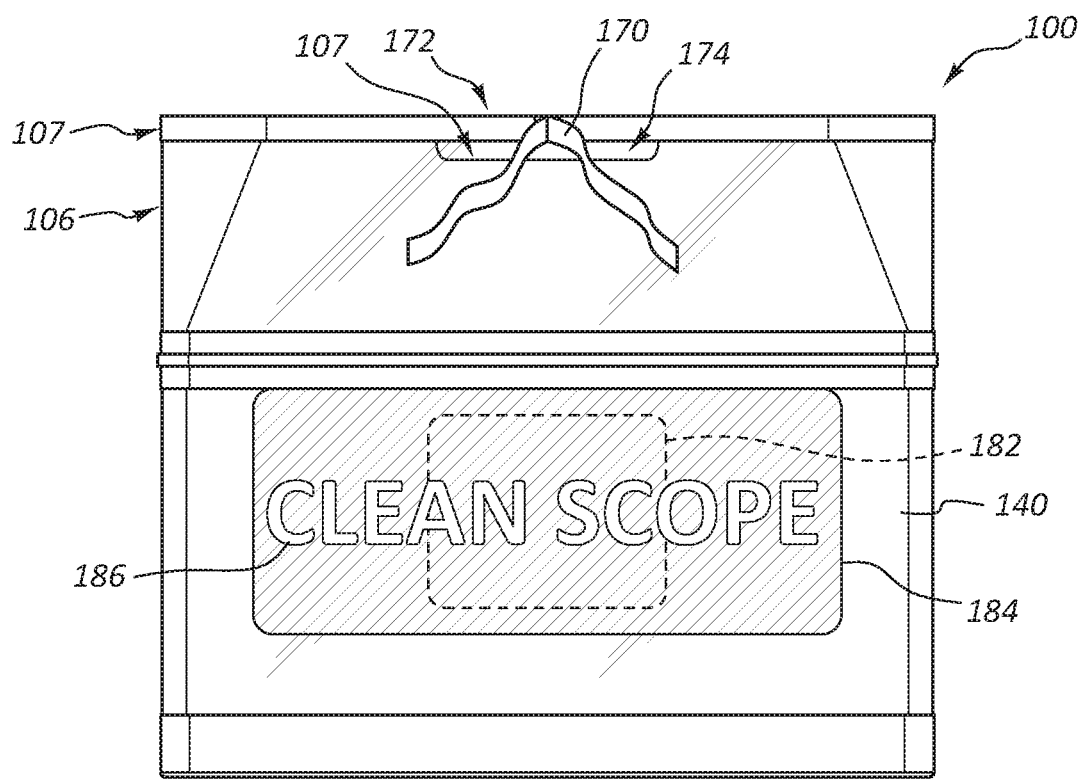
FIG. 4A is an end view of the medical device transport container of FIG. 1 in a first configuration.
Figure 4B:
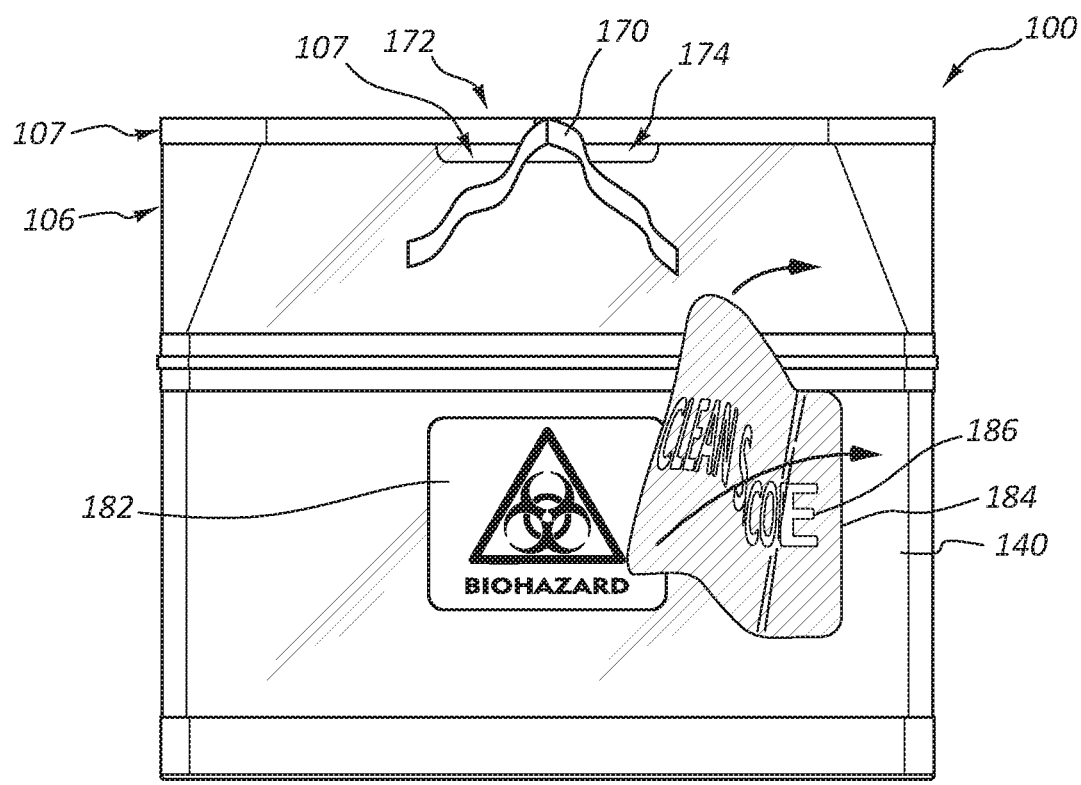
FIG. 4B is an end view of the medical device transport container of FIG. 1 in a second configuration.

FIGS. 4A and 4B are end views of the container 100 of FIG. 1 in a first configuration and a second configuration, respectively. In some embodiments, the container 100 may comprise a first indicium 182 disposed on at least a portion of the container 100. As illustrated, the first indicium 182 can be disposed on at least a portion of an exterior surface of the container 100. The first indicium 182 may also be disposed on other portions of the container 100. The first indicium 182 may indicate to a user that at least one content (e.g., a medical device) of the container 100 is in a first state. The container 100 may further comprise a removable label 184 comprising a second indicium 186. In some embodiments, the removable label 184 may be green or another suitable color. The second indicium 186 may indicate to the user that the at least one content of the container 100 is in a second state. As illustrated, the removable label 184 may be configured to be replaceably disposed over at least a portion of the first indicium 182. For example, the first state may be a contaminated state. In such a configuration the first indicium 182 may comprise a biohazard symbol, as illustrated. Any other suitable first indicium or symbol is also within the scope of this disclosure. In some embodiments, at least a portion of the first indicium may be red or another suitable color. The second state may be a clean state. In such a configuration the second indicium 186 may comprise the words "clean scope," as illustrated. Any other suitable second indicium or symbol is also within the scope of this disclosure.

In certain embodiments, the removable label 184 may be coupled to the container 100 by an adhesive, a hook and loop fastener, etc. In some embodiments, the removable label 184 may be replaceably coupleable to the container 100. In some other embodiments, the removable label 184 may be configured to be coupled only once to the container 100 and may be discarded upon removal of the removable label 184 from the container 100.

The closing member 170 is also depicted in FIGS. 4A and 4B. As depicted, the closing member 170 comprises a drawstring. In some embodiments, each of the closing member 170 and the upper edge 107 or the upper portion 106 of the container 100 may cooperate to form at least two handles 172. For example, a handle opening 174 may be defined by a portion of the upper edge 107 of the container 100 and the closing member 170. The one or more handles 172 may be configured to be grasped or held by a user. For example, a user may dispose one or more of his or her fingers through the one or more handle openings 174 and grasp the one or more portions of the closing member 170 disposed adjacent the handle openings 174.

Figure 5:
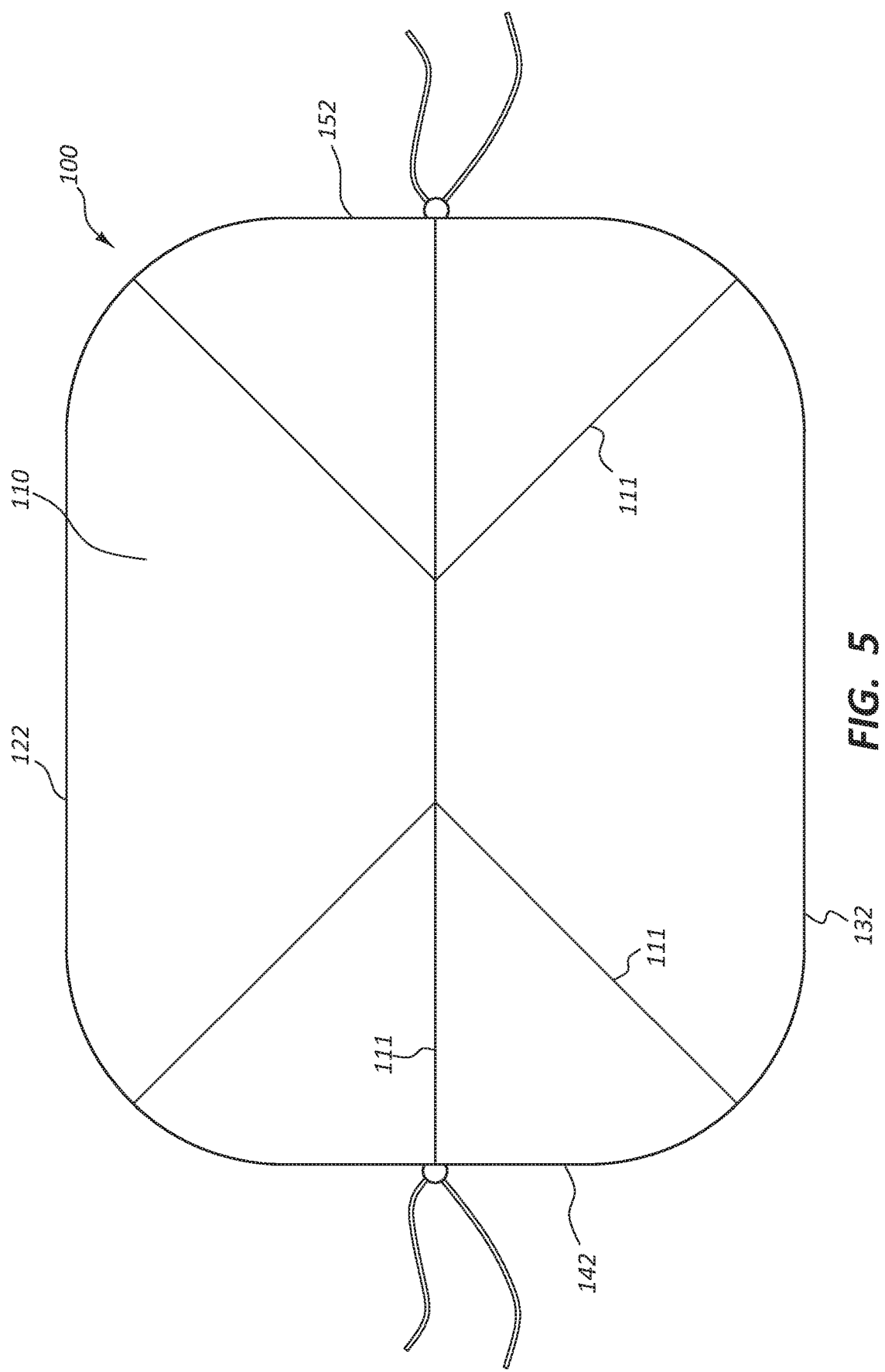
FIG. 5 is a bottom view of the medical device transport container of FIG. 1.

FIG. 5 is a bottom view of the container 100. The lower panel 110 can be disposed at the base or bottom of the container 100 and may comprise one or more folds 111. In the illustrated embodiment, the material used to form the lower panel 110 can be folded in a manner such that a single piece of material may be used to form the first panel, the second panel, the first side panel, the second side panel, and/or the lower panel 110 of the container 100. Other configurations of the lower panel 110 are also within the scope of the present disclosure. For example, the lower panel 110 may lack any folds such as the folds 111 depicted in FIG. 5. In some embodiments, the lower panel 110 may comprise a single piece of material that is coupled to each of the lower panel edges 122, 132, 142, 152, of the each of the first panel, the second panel, the first side panel, and/or the second side panel, respectively. Additionally, the lower panel 110 may be flat for placement or standing of the container 100 on a surface.

Figure 6:
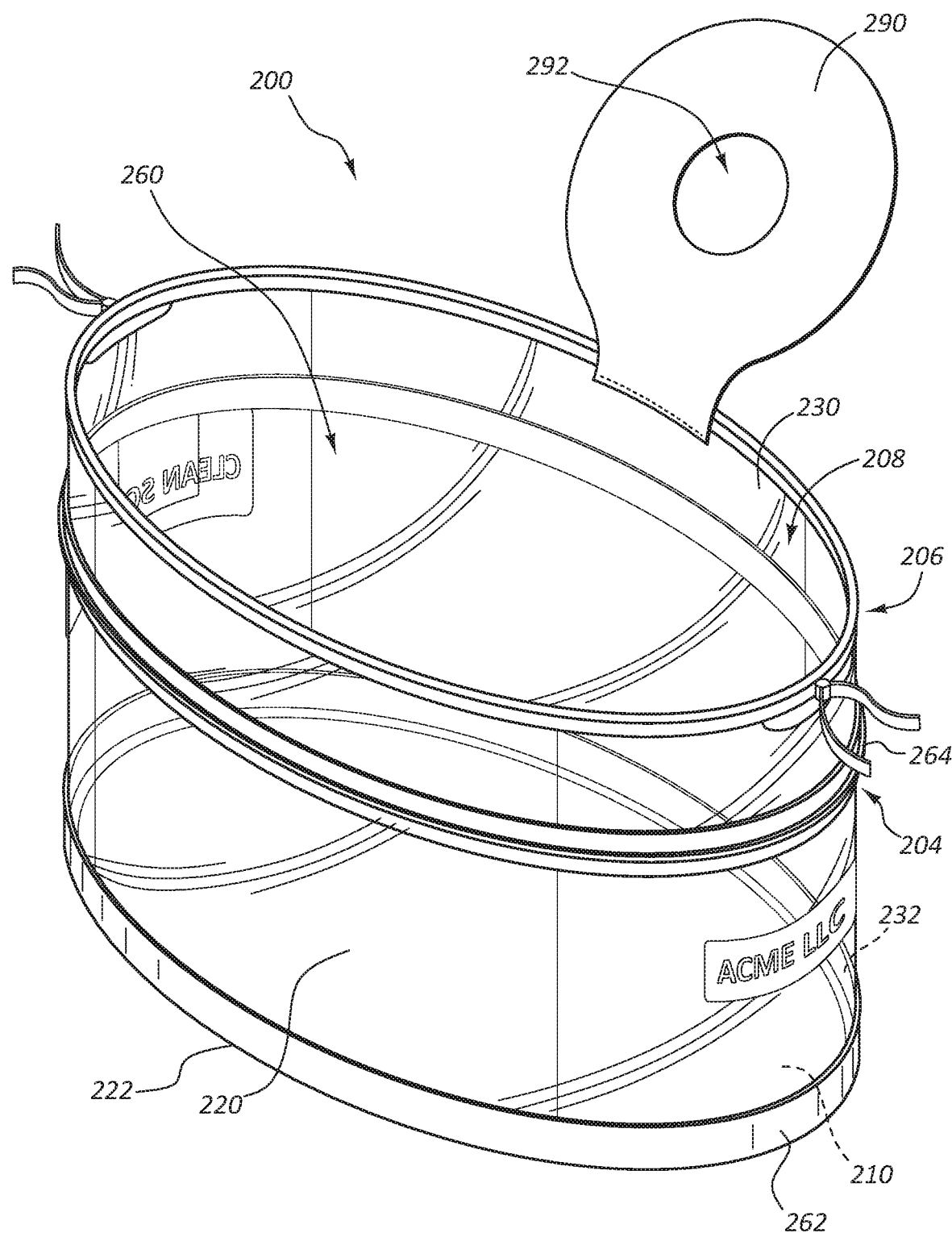
FIG. 6 is a perspective view of another embodiment of a medical device transport container.

FIG. 6 illustrates another embodiment of a medical device transport container that can, in certain respects, resemble components of the medical device transport container described in connection with FIGS. 1-5. It will be appreciated that all the illustrated embodiments may have analogous features. Accordingly, like features are designated with like reference numerals, with the leading digits incremented to "2." For instance, the first panel is designated as "120" in FIGS. 1-5, and an analogous first panel is designated as "220" in FIG. 6. Relevant disclosure set forth above regarding similarly identified features thus may not be repeated hereafter. Moreover, specific features of the medical device transport container and related components shown in FIGS. 1-5 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical device transport container of FIG. 6. Any suitable combination of the features, and variations of the same, described with respect to the medical device transport container and components illustrated in FIGS. 1-5 can be employed with the medical device transport container and components of FIG. 6, and vice versa. This pattern of disclosure applies equally to further embodiments depicted in subsequent figures and described hereafter.

FIG. 6 is a perspective view of a medical device transport container 200. As depicted, the container 200 may comprise a first panel 220 disposed opposite of a second panel 230. The container 200 can also comprise a lower panel 210, wherein the lower panel 210 is coupled to a lower edge or lower panel edge 222, 232 of each of the first panel 220 and the second panel 230, respectively. As illustrated, each of the lower panel 210, the first panel 220, and the second panel 230 can cooperate to form a cavity 260.

The container 200 can further comprise a first band member 264 disposed along at least a portion of a circumference of the cavity 260. The first band member 264 may be coupled to a middle portion 204 of the each of the first panel 220 and the second panel 230. The container 200 can further comprise a second band member 262 disposed along at least a portion of the circumference of the cavity 260. The second band member 262 may be coupled adjacent the lower edge 222, 232 of each of the first panel 220 and the second panel 230. In certain embodiments, each of the first panel 220, the second panel 230, and the lower panel 210 may be integral. In certain other embodiments, one or more of the first panel 220, the second panel 230, and/or the lower panel 210 may be independent or separate.

As illustrated, the container 200 can further comprise a hang tab or flap member 290. The flap member 290 may be integral with or coupled to an upper portion 206 of the container 200. Furthermore, the flap member 290 may be disposed adjacent an opening 208 of the container 200. The flap member 290 may be configured to removably couple the container 200 to a medical device. For example, the flap member 290 may comprise an aperture or opening 292, wherein the aperture 292 is disposed through at least a portion of the flap member 290. The aperture 292 may be configured for the passage of at least a portion of a medical device. For example, the medical device may be an elongate medical device such as an endoscope. A portion of the endoscope may pass through at least a portion of the aperture 292. In some embodiments, the flap member 290 may be configured to couple the container 200 to an object such as a hook, such that the container 200 may be disposed in a hanging configuration.

The flap member 290 may also be configured to be disposed over at least a portion of the opening 208 of the container 200. In such a configuration, the flap member 290 may aid in the transition of the opening 208 to the closed configuration. For example, the flap member may fold over at least a portion of the opening 208 and prevent or inhibit flow or passage of one or more contents of the container 200 out of the container 200. Analogously, the flap member 290, when the container 200 is in the closed configuration, may prevent or inhibit the flow or passage of one or more objects from an exterior of the container 200 into the cavity 260 of the container 200.

In various other embodiments, a container assembly may comprise a first container coupled to a second container. The first container may comprise a first color (e.g., green or another suitable color) and the second container may comprise a second color (e.g., red or another suitable color). In a first configuration, the second container may be disposed in a folded or packaged configuration and may be disposed at or adjacent a lower panel or a lower portion of the first container. In some embodiments, the second container may be disposed within a storage compartment that is coupled to the lower panel or the lower portion of the first container. The second container may also comprise a deployment mechanism. In some embodiments, a practitioner may activate or grasp the deployment mechanism such that the second container may deploy or unfold along at least a portion of an exterior surface of the first container such that the container assembly transitions from a first configuration (i.e., wherein the second container is folded or disposed within a storage compartment) to a second configuration (i.e., wherein the second container is deployed or unfolded and disposed over the exterior surface of the first container).

When the container assembly is in the first configuration a clean or sterile medical device may be disposed or secured within a portion of the first container. As discussed above, the first container may be green and the green color may indicate to a practitioner that the medical device disposed within the container assembly is clean or uncontaminated. After the medical device has been used (e.g., during a medical procedure) the medical device may be dirty or contaminated and the practitioner may dispose the medical device within the first container. The practitioner may then activate or deploy the second container (i.e., via the deployment mechanism) to transition the container assembly to the second configuration and the second container may deploy around a portion of the exterior surface of the first container. As discussed above, the second container may be red and the red color may indicate to the practitioner that the medical device disposed within the container assembly is dirty or contaminated. Other configurations or combinations of the components of the container assembly are also within the scope of this disclosure.

Figure 7A:
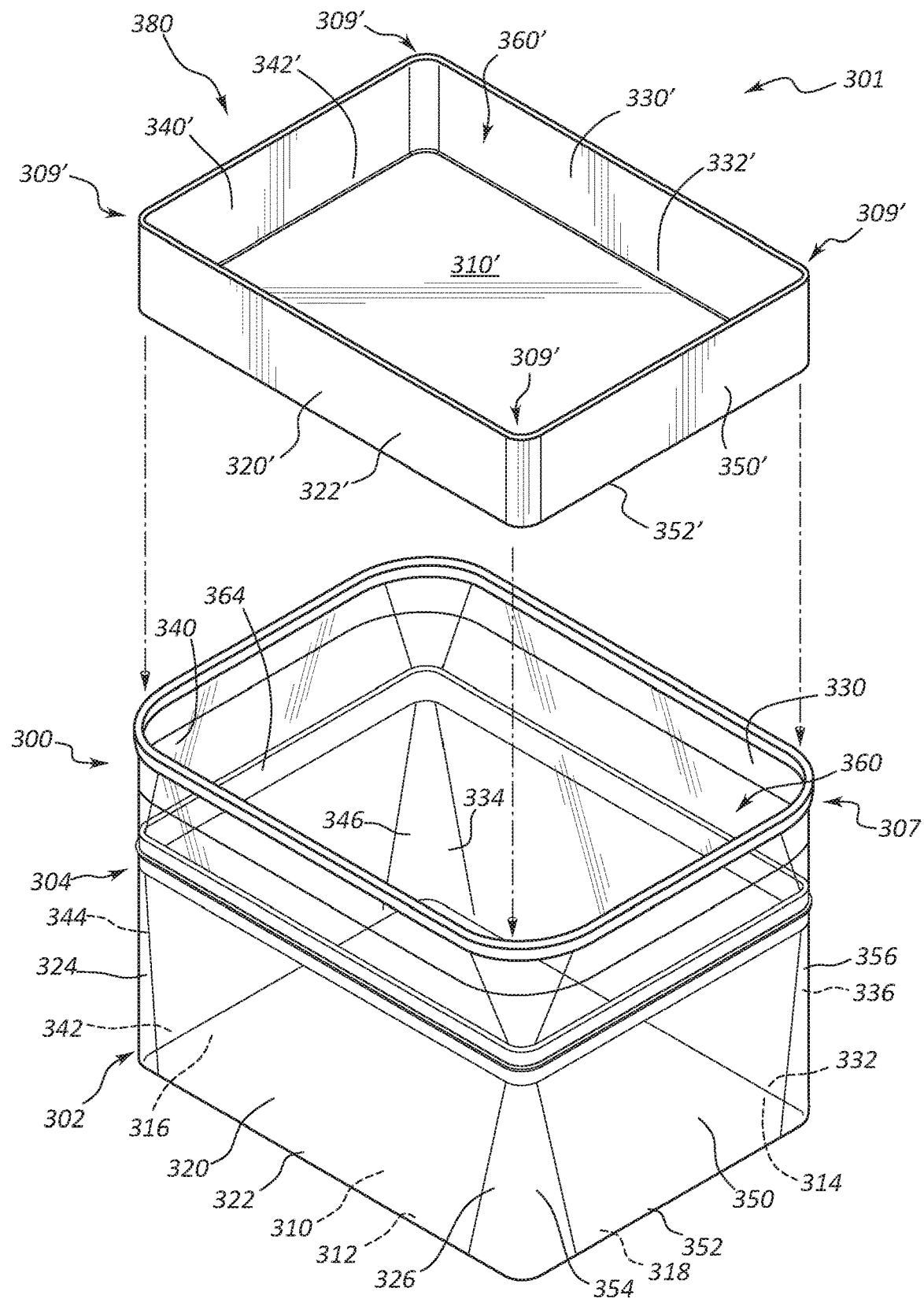
FIG. 7A is an exploded perspective view of an embodiment of a medical device transport container system.
Figure 7B:
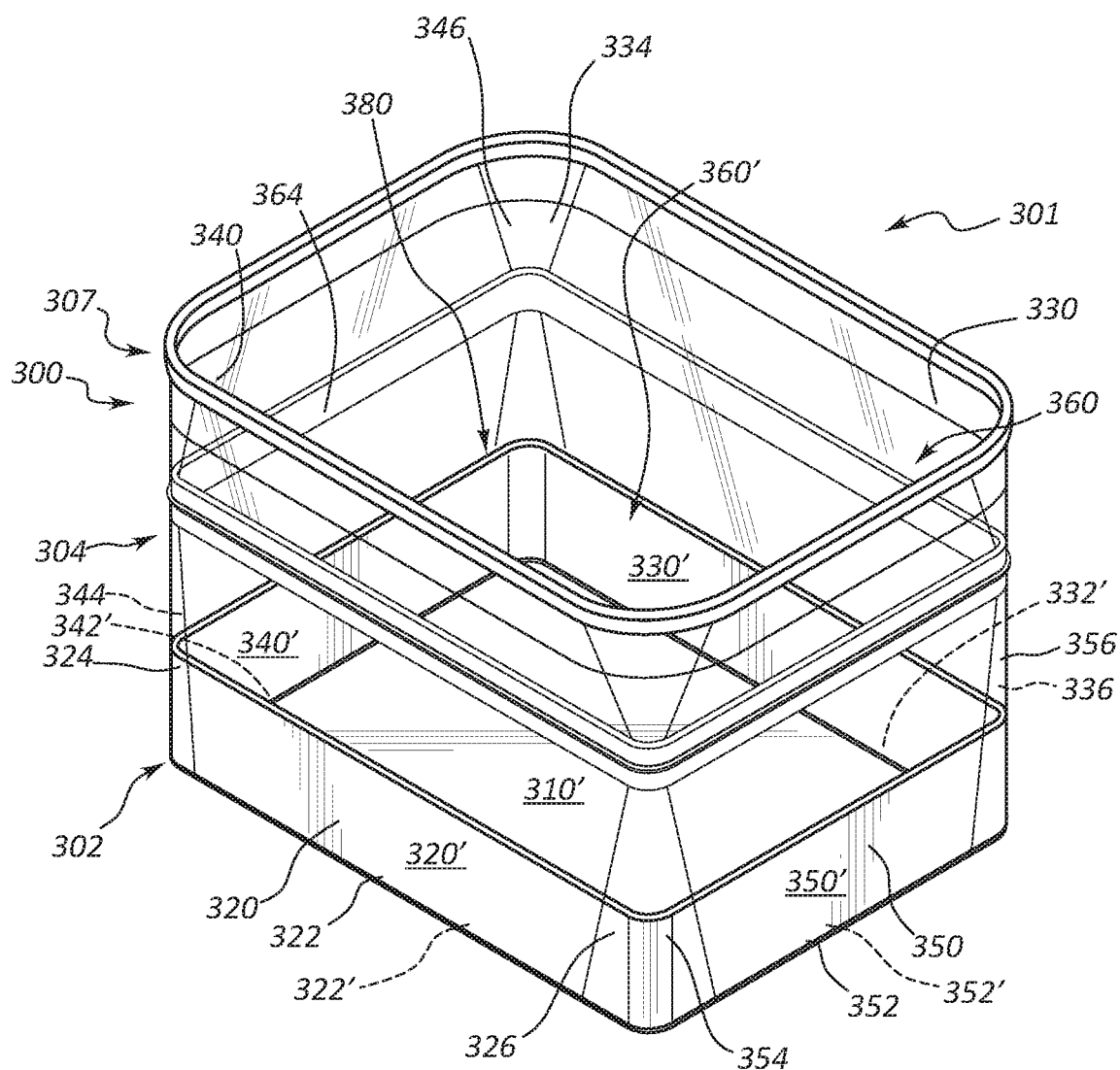
FIG. 7B is a perspective view of the medical device transport container system of FIG. 7A in an assembled configuration.

FIGS. 7A and 7B provide alternative views of a medical device transport container system 301 comprising an outer container 300 that resembles the medical device transport containers 100, 200 described above in certain respects. As noted above, relevant disclosure set forth above regarding similarly identified features of the medical device transport containers 100, 200 may not be repeated in reference to the medical device transport container system 301 and the outer container 300. However, such features may clearly be the same, or substantially the same, as features depicted in other embodiments and/or described with respect to such embodiments. Accordingly, the relevant descriptions of such features apply equally to the features of the medical device transport container system 301, the outer container 300, and related components depicted in FIGS. 7A and 7B. Furthermore, any suitable combination of the features, and variations of the same, described with respect to the medical device transport containers 100, 200 and related components illustrated in FIGS. 1-6 can be employed with the medical device transport container system 301, the outer container 300, and related components of FIGS. 7A and 7B, and vice versa.

FIG. 7A is an exploded view of the medical device transport container system 301 depicting the outer container 300 and an insert portion 380. Furthermore, FIG. 7B is a perspective view of the medical device transport container system 301 wherein the insert portion 380 is disposed within and/or coupled to the outer container 300 (i.e., in an assembled configuration). In some embodiments, the insert portion 380 may be fixedly coupled to the outer container 300. For example, the insert portion 380 may be adhered (e.g., via an adhesive) to the outer container 300. In some other embodiments, the insert portion 300 may be configured to be removably coupled to the outer container 300. For example, the insert portion 380 may be disposable (i.e., a single-use insert portion) while the outer container 300 may be reusable (i.e., a reusable outer container). That is, the insert portion 380 may become contaminated during use of the container system 301, and a user may remove and/or discard the contaminated insert portion 380 and couple or dispose a new (i.e., uncontaminated) insert portion 380 to or within a reused outer container 300. Embodiments wherein the insert portion 380 is reusable, the outer container 300 is disposable, each of the insert portion 380 and the outer container 300 is reusable, or each of the insert portion 380 and the outer container 300 is disposable are also within the scope of this disclosure.

The insert portion 380 may be coupled to the outer container 300 by a variety of mechanisms. For example, the insert portion 380 may be coupled to the outer container 300 by one or more of the following: snaps, latches, zippers, hook and loop fasteners, buttons, hook and eye closures, adhesives, and/or another suitable coupling mechanism.

The outer container 300 comprises a first panel, first container panel, or front panel 320 disposed substantially opposite of a second panel, second container panel, or rear panel 330. Additionally, the outer container 300 comprises a first side panel or first container side panel 340 extending or disposed between each of the first panel 320 and the second panel 330. A second side panel or second container side panel 350 is disposed substantially opposite of the first side panel 340, and the second side panel 350 extends or is disposed between each of the first panel 320 and the second panel 330.

The outer container 300 can further comprise a lower panel or lower container panel 310. The shape of the lower panel 310, as illustrated, is substantially rectangular. In some other embodiments, the shape of the lower panel 310 may be substantially square, substantially circular, substantially oval, etc. Any other suitable shape can also be used. For example, the shape of the lower panel 310 of the outer container 300 can be non-rectangular and/or irregular (i.e., not a traditionally defined shape).

The lower panel 310 can be coupled to a lower edge or lower panel edge 322, 332, 342, 352 of the first panel 320, the second panel 330, the first side panel 340, and/or the second side panel 350, respectively. As depicted in FIGS. 7A and 7B, each of the lower panel 310, the first panel 320, the second panel 330, the first side panel 340, and the second side panel 350 can cooperate to form at least a portion of a cavity, container cavity, or void 360 within at least a portion of an interior of the outer container 300. In some embodiments, the outer container 300 may only comprise a subset of the panels (e.g., only a first panel 320 and a second panel 330), and the subset of panels may likewise cooperate to form the cavity 360.

As discussed above in reference to container 100, also within the scope of the present disclosure are containers comprising a single geometrically continuous wall or panel, for example, wherein a single panel is disposed in a continuous arc or curve, such as a bag comprising a continuous circular wall. The first panel, second panel, first side panel, second side panel, and/or lower panel, as described herein, may thus be understood as referring to portions of a single continuous wall or panel. In some embodiments, such portions may be integral and may not be divided or separated by seams, corners, or other components of the single geometrically continuous panel.

The cavity 360 may be configured to receive and retain a medical device, such as an endoscope. Other contents of the cavity 360 are also within the scope of this disclosure. In certain embodiments, the outer container 300 may be configured to protect a content of the outer container 300. For example, the outer container 300 may inhibit or prevent a medical device that is retained within the cavity 360 from being broken or damaged. The outer container 300 may also isolate a clean medical device such that the clean medical device is inhibited or prevented from becoming contaminated. Likewise, the outer container 300 may isolate a contaminated medical device such that the contaminated medical device is inhibited or prevented from contaminating objects that are exterior of the outer container 300.

In some embodiments, the outer container 300 may further comprise a band member or first band member 364. The band member 364 may comprise an absorbent material, and/or the band member 364 may be coupled to an absorbent material. Embodiments wherein the band member 364 does not comprise an absorbent material or wherein the band member 364 is not coupled to an absorbent material are also within the scope of the present disclosure. As illustrated, the band member 364 may be disposed along at least a portion of a circumference of the cavity 360. The band member 364 may be coupled to or disposed along a middle portion 304 of each of the first panel 320, the second panel 330, the first side panel 340, and/or the second side panel 350. Analogously, in embodiments wherein the outer container 300 comprises only a subset of the panels or only a single panel, the band member 364 may be coupled to or disposed along the middle portion 304 of the subset of panels or the single panel.

In certain embodiments, the outer container 300 may comprise another number of band members, analogous to the band member 364. For example, the outer container 300 may comprise one, two, three, four, five, or more band members. For example, a second band member may be disposed above the band member 364. The second band member may extend along at least a portion of an upper edge 307 of the outer container 300. Other configurations of the band members are also within the scope of this disclosure.

In various embodiments, the height of the band member 364 may be about 0.1 inches to about 4 inches. In various other embodiments, the height of the band member 364 may be about 0.5 inches to about 3.5 inches, about 1 inch to about 3 inches, about 1.5 inches to about 2.5 inches, or about 2 inches. Any other suitable height of the band member 364 is also within the scope of this disclosure.

In some embodiments, one or more of the components of the outer container 300 may be integral. For example, each of the first panel 320 and the second side panel 350 may be formed from a single piece of material. In certain embodiments, each of the lower panel 310, the first panel 320, the second panel 330, the first side panel 340, and the second side panel 350 can be integral. In some other embodiments, one or more of the components of the outer container 300 may be independent or separate. For example, the first panel 320 may be formed from a first piece of material and the second side panel 350 may be formed from a second piece of material.

In some embodiments, the length of the outer container 300 may be about 8 inches to about 30 inches. In some other embodiments, the length of the outer container 300 may be about 10 inches to about 28 inches, about 12 inches to about 26 inches, about 14 inches to about 24 inches, about 16 inches to about 26 inches, or about 18 inches to about 20 inches. Any other suitable length of the outer container 300 is also within the scope of this disclosure. In some embodiments, the width of the outer container 300 may be about 8 inches to about 21 inches. In some other embodiments, the width of the outer container 300 may be about 10 inches to about 19 inches, about 12 inches to about 17 inches, or about 14 inches to about 15 inches. Any other suitable width of the outer container 300 is also within the scope of this disclosure. In some embodiments, the height of the outer container 300 may be about 6 inches to about 18 inches. In some other embodiments, the height of the outer container 300 may be about 8 inches to about 16 inches, about 10 inches to about 14 inches, or about 12 inches. Any other suitable height of the outer container 300 is also within the scope of this disclosure.

With continued reference to FIGS. 7A and 7B, the first panel 320 can comprise the lower panel edge 322 that may be coupled to a first panel edge 312 of the lower panel 310. The first panel 320 can further comprise a first side panel edge 324 disposed opposite of a second side panel edge 326. Analogous to the first panel 320, the second panel 330 can comprise the lower panel edge 332. The lower panel edge 332 can be coupled to a second panel edge 314 of the lower panel 310. The second panel 330 can further comprise a first side panel edge 334 disposed opposite of a second side panel edge 336.

The first side panel 340, as illustrated, can comprise a first panel edge 344 that can be coupled to the first side panel edge 324 of the first panel 320. Analogously, a second panel edge 346 of the first side panel 340 can be coupled to the first side panel edge 334 of the second panel 330. Furthermore, the first side panel 340 can comprise the lower panel edge 342 that can be coupled to a first side panel edge 316 of the lower panel 310.

The second side panel 350 can comprise a first panel edge 354 that can be coupled to the second side panel edge 326 of the first panel 320. Furthermore, the second side panel 350 can comprise a second panel edge 356 that can be coupled to the second side panel edge 336 of the second panel 330. The second side panel 350 can also comprise the lower panel edge 352 that can be coupled to a second side panel edge 318 of the lower panel 310.

As depicted, the outer container 300 may be configured to stand upright. In other words, the outer container 300 may be capable of standing on its own. The outer container 300 may also be substantially capable of maintaining its structural conformation. In certain embodiments, the lower panel 310 of the outer container 300 may serve as a base on which the outer container 300 rests. The first panel 320, the second panel 330, the first side panel 340, and/or the second side panel 350 may extend upwardly from the lower panel 310. The first panel 320, the second panel 330, the first side panel 340, and/or the second side panel 350 may also be attached or otherwise directly coupled to the lower panel 310. In other embodiments, one or more of the first panel 320, the second panel 330, the first side panel 340, and/or the second side panel 350 may be integrally formed with the lower panel 310. For example, each of the first panel 320, the second panel 330, the first side panel 340, and the second side panel 350 may be formed from a single piece of material.

Analogous to the outer container 300, the insert portion 380 comprises a first panel, first insert panel, or front panel 320' disposed substantially opposite of a second panel, second insert panel, or rear panel 330'. Additionally, the insert portion 380 comprises a first side panel or first insert side panel 340' extending or disposed between each of the first panel 320' and the second panel 330'. A second side panel or second insert side panel 350' is disposed substantially opposite of the first side panel 340', and the second side panel 350' extends or is disposed between each of the first panel 320' and the second panel 330'. The insert portion 380 can further comprise a lower panel or lower insert panel 310'.

In some embodiments, one or more of the lower panel 310', the first panel 320', the second panel 330', the first side panel 340', and/or the second side panel 350' comprises an absorbent material and/or can be formed from an absorbent material. The absorbent material may be selected from one or more of a polymer, a fabric, or another suitable absorbent material. The absorbent material and/or the insert portion 380 formed from the absorbent material may be configured to absorb one or more fluids. For example, a fluid may flow into or be disposed within a portion of a cavity or insert cavity 360' of the insert portion 380 and the absorbent material and/or the insert portion 380 formed from the absorbent material may be configured to absorb at least a portion of the fluid.

In various embodiments, at least a portion of the material forming one or more of the lower panel 310', the first panel 320', the second panel 330', the first side panel 340', and/or the second side panel 350' may be coated, contained, partially sealed, and/or treated. For example, at least a portion of the material may be treated such that one or more portions of the material (e.g., particles of the material) are not dislodged (e.g., onto an endoscope) during use of the container system 301. In some embodiments one or more surfaces of the lower panel 310', the first panel 320', the second panel 330', the first side panel 340', and/or the second side panel 350' may comprise a semipermeable barrier layer, allowing liquid to be absored by the panels while preventing particles or portions of the material from sticking to an endoscope. One or more portions of the materials forming other portions of the containers and/or container systems of the present disclosure may also be analogously coated, sealed, and/or treated.

In various embodiments, the insert portion 380 may be configured to inhibit or prevent fluid flow from within at least a portion of the cavity 360 of the outer container 300 and/or at least a portion of the cavity 360' of the insert portion 380 to a position exterior of the container system 301, the outer container 300, and/or the insert portion 380. For example, a fluid may be disposed or present in the insert portion 380. The container system 301 may be tipped onto its side (i.e., on to one of the first panel 320, the second panel 330, the first side panel 340, or the second side panel 350) resulting in the flow of the fluid from within the cavity 360 of the outer container 300 and/or the cavity 360' of the insert portion 380 toward a position exterior of the container system 301, the outer container 300, and/or the insert portion 380. The insert portion 380 may be configured to absorb at least a portion of the fluid such that the absorbed fluid does not flow out of the cavity 360 of the outer container 300 and/or the cavity 360' of the insert portion 380.

In certain embodiments, the lower panel 310' may be coupled to (e.g., directly coupled to) the lower panel 310 of the outer container 300 (see FIG. 7B). In certain other embodiments, the lower panel 310' may be configured to be disposed against the lower panel 310' of the outer container 300. As illustrated, the shape of the insert portion 380 and the lower panel 310' of the insert portion 380 is substantially rectangular. In some other embodiments, the shape of the insert portion 380 and/or the lower panel 310' may be substantially square, substantially circular, substantially oval, etc. Any other suitable shape can also be used. For example, the shape of the insert portion 380 and/or the lower panel 310' can be non-rectangular and/or irregular (i.e., not a traditionally defined shape). In various embodiments, the shape and/or the size of the insert portion 380 and/or the lower panel 310' may be configured to substantially correspond with the shape and/or the size of the outer container 300 and/or the lower panel 310. For example, the insert portion and the later panel 310' may be configured, shaped, and/or sized to fit within the outer container 300.

The lower panel 310' can be coupled to a lower edge or lower panel edge 322', 332', 342', 352' of the first panel 320', the second panel 330', the first side panel 340', and/or the second side panel 350', respectively. As depicted in FIGS. 7A and 7B, each of the lower panel 310', the first panel 320', the second panel 330', the first side panel 340', and the second side panel 350' can cooperate to form at least a portion of the cavity, insert cavity, or void 360' within at least a portion of an interior of the insert portion 380. In some embodiments, the insert portion 380 may only comprise a subset of the panels (e.g., only a first panel 320' and a second panel 330'), and the subset of panels may likewise cooperate to form the cavity 360'.

In some embodiments, one or more portions or sections of the outer container 300 may be weighted. The weighted portions of the outer container 300 may be disposed at or adjacent one or more positions wherein the lower panel 310 is coupled to one or more of the lower edges 322, 332, 342, 352 of the first panel 320, the second panel 330, the first side panel 340, and/or the second side panel 350, respectively. For example, one or more weights may be coupled to or disposed within at least a portion of the outer container 300 such that the outer container 300 may rest flatly on a surface (e.g., on a counter, a table, etc.). Further, the weighted portions of the outer container 300 may be formed from a heavy material and/or a material that has been folded one or more times on itself (i.e., so as to provide one or more portions of the outer container 300 with additional heft).

Likewise, one or more portions or sections of the insert portion 380 may be weighted. The weighted portions of the insert portion 380 may be disposed at or adjacent one or more positions wherein the lower panel 310' is coupled to the lower edges 322', 332', 342', 352' of the first panel 320', the second panel 330', the first side panel 340', and/or the second side panel 350', respectively. Analogous portions or sections of the container system 301 may also be weighted, for example, such that the container system 301 may be configured to rest flatly on a surface.

As discussed above regarding the containers 100, 300, insert portions comprising a single geometrically continuous wall or panel, for example, wherein a single panel is disposed in a continuous arc or curve, such as a bag comprising a continuous circular wall are also within the scope of this disclosure. The first panel, second panel, first side panel, second side panel, and/or lower panel, as described herein, may thus be understood as referring to portions of a single continuous wall or panel. In some embodiments, such portions may be integral and may not be divided or separated by seams, corners, or other components of the single geometrically continuous panel. Stated another way, in some embodiments, one or more of the components of the insert portion 380 may be integral. In some other embodiments, one or more of the components of the insert portion 380 may be independent or separate.

The cavity 360' may be configured to receive and retain a medical device, such as an endoscope. Other contents of the cavity 360' are also within the scope of this disclosure. In certain embodiments, the insert portion 380 may be configured to protect a content of the insert portion 380 and/or the outer container 300. For example, the insert portion 380 may inhibit or prevent a medical device that is retained within the cavity 360' from being broken or damaged. In various embodiments, an endoscope may be disposed in the cavity 360' of the insert portion 380. The absorbent material forming the insert portion 380 may cushion or otherwise protect the endoscope. For example, a lens of the endoscope may be fragile, and the insert portion 380 and/or the absorbent material forming the insert portion 380 may protect the lens of the endoscope such that the lens is prevented or protected from being cracked, scratched, or otherwise damaged.

As illustrated in FIGS. 7A and 7B, the first panel 320', the second panel 330', the first side panel 340', and/or the second side panel 350' may extend upward from the lower panel 310'. In such a configuration, one or more portions or components of the endoscope that may be disposed in the outer container 300 and/or the insert portion 380 (e.g., a lens of the endoscope) may come into contact with the interior surfaces of the panels of the insert portion 380. Accordingly, the absorbent material forming the first panel 320', the second panel 330', the first side panel 340', the second side panel 350', and/or the lower panel 310' of the insert portion 380 may prevent or protect the lens of the endoscope from being cracked, scratched, or otherwise damaged.

The insert portion 380 may tend to maintain its shape, including embodiments where it is substantially rigid or stiff. For example, the insert portion 380 may be formed from a material that is more rigid than the materials from which one or more of the first panel 320, the second panel 330, the first side panel 340, and/or the second side panel 350 of the outer container 300 are formed. Likewise, in embodiments of the outer container 300 comprising only a single continuous panel or a subset of the panels 320, 330, 340, 350, the insert portion 380 may be formed from a material that is more rigid than the materials from which the single continuous panel or the subset of panels are formed. Consequently, the insert portion 380 may be configured to support or reinforce at least a portion of the outer container 300 (e.g., a lower portion 302 of the outer container 300).

In various embodiments, the height of the insert portion 380 (i.e., the height of the first panel 320', the second panel 330', the first side panel 340', and/or the second side panel 350') may be about 0.5 inch to about 15 inches. In various other embodiments, the height of the insert portion may be about 1 inch to about 12 inches, about 2 inches to about 10 inches, about 2.5 inches to about 8 inches, or about 3 inches. Any other suitable height of the insert portion 380 is also within the scope of this disclosure. In various other embodiments, when the insert portion 380 is disposed in the outer container 300, the first panel 320', the second panel 330', the first side panel 340', and/or the second side panel 350' of the insert portion 380 may extend upwards along at least about two-thirds of the height of the outer container 300, at least about half of the height of the outer container 300, at least about one-third of the height of the outer container 300, at least about one-fourth of the height of the outer container 300, or another suitable fraction of the height of the outer container 300.

As discussed above, the insert portion 380 may be configured to be disposed within and/or coupled to the outer container 300. Accordingly, the insert portion 380 can be dimensioned or sized such that the insert portion 380 may be disposed within at least a portion of the cavity 360 of the outer container 300 (e.g., within the lower portion 302 of the cavity 360 of the outer container 300). For example, the length and/or the width of the insert portion 380 may be less than the length and/or the width, respectively, of the outer container 300. In some embodiments, the fit between the inner surface of the outer container 300 and the outer surface of the insert portion 380 may be substantially snug or tight when the insert portion 380 is disposed within the outer container 300. In some other embodiments, the fit between the inner surface of the outer container 300 and the outer surface of the insert portion 380 may be substantially loose when the insert portion 380 is disposed within the outer container 300.

In some embodiments, the length of the insert portion 380 may be about 8 inches to about 30 inches. In some other embodiments, the length of the insert portion 380 may be about 10 inches to about 28 inches, about 12 inches to about 26 inches, about 14 inches to about 24 inches, about 16 inches to about 26 inches, or about 18 inches to about 20 inches. Any other suitable length of the insert portion 380 is also within the scope of this disclosure. In some embodiments, the width of the insert portion 380 may be about 8 inches to about 21 inches. In some other embodiments, the width of the insert portion 380 may be about 10 inches to about 19 inches, about 12 inches to about 17 inches, or about 14 inches to about 15 inches. Any other suitable width of the insert portion 380 is also within the scope of this disclosure.

In certain embodiments, at least a portion of one or more of each of the first panel 320', the second panel 330', the first side panel 340', and/or the second side panel 350' may tend to hold a shape, including embodiments wherein it is substantially rigid, such that at least a portion of the insert portion 380 is configured to stand substantially upright. In some embodiments, one or more support members (not shown) may be coupled to one or more portions of the insert portion 380. For example, at least one elongate support member may be coupled at or adjacent at least a portion of at least one corner 309' of the insert portion 380. In some embodiments, one or more support members may be coupled to at least one corner 309', at least two corners 309', at least three corners 309', at least four corners 309', etc. of the insert portion 380. One or more support members may also be coupled to one or more other suitable portions of the insert portion 380.

As described above in reference to the containers 100, 300, the lower panel 310', the first panel 320', the second panel 330', the first side panel 340', and/or the second side panel 350' may be coupled at multiple positions. The lower panel 310', the first panel 320', the second panel 330', the first side panel 340', and/or the second side panel 350' may be coupled by a variety of mechanisms, for example, by a seam. The seam may comprise a seal, such as a heat seal. In some embodiments, the seam may be formed via an adhesive, stitching, or any other suitable method. The seam may or may not be airtight and/or liquid-tight.

Figure 8A:
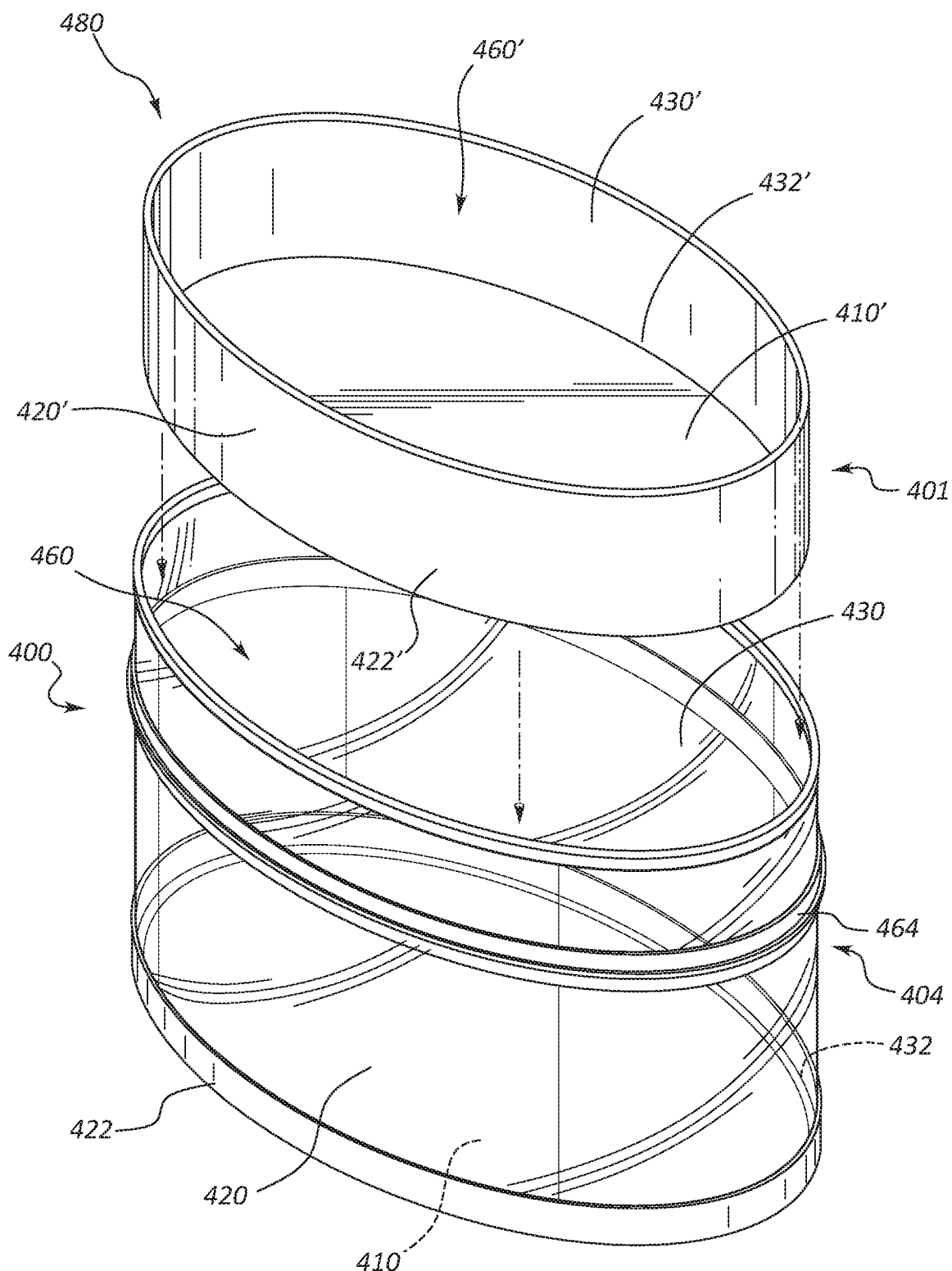
FIG. 8A is an exploded perspective view of another embodiment of a medical device transport container system.
Figure 8B:
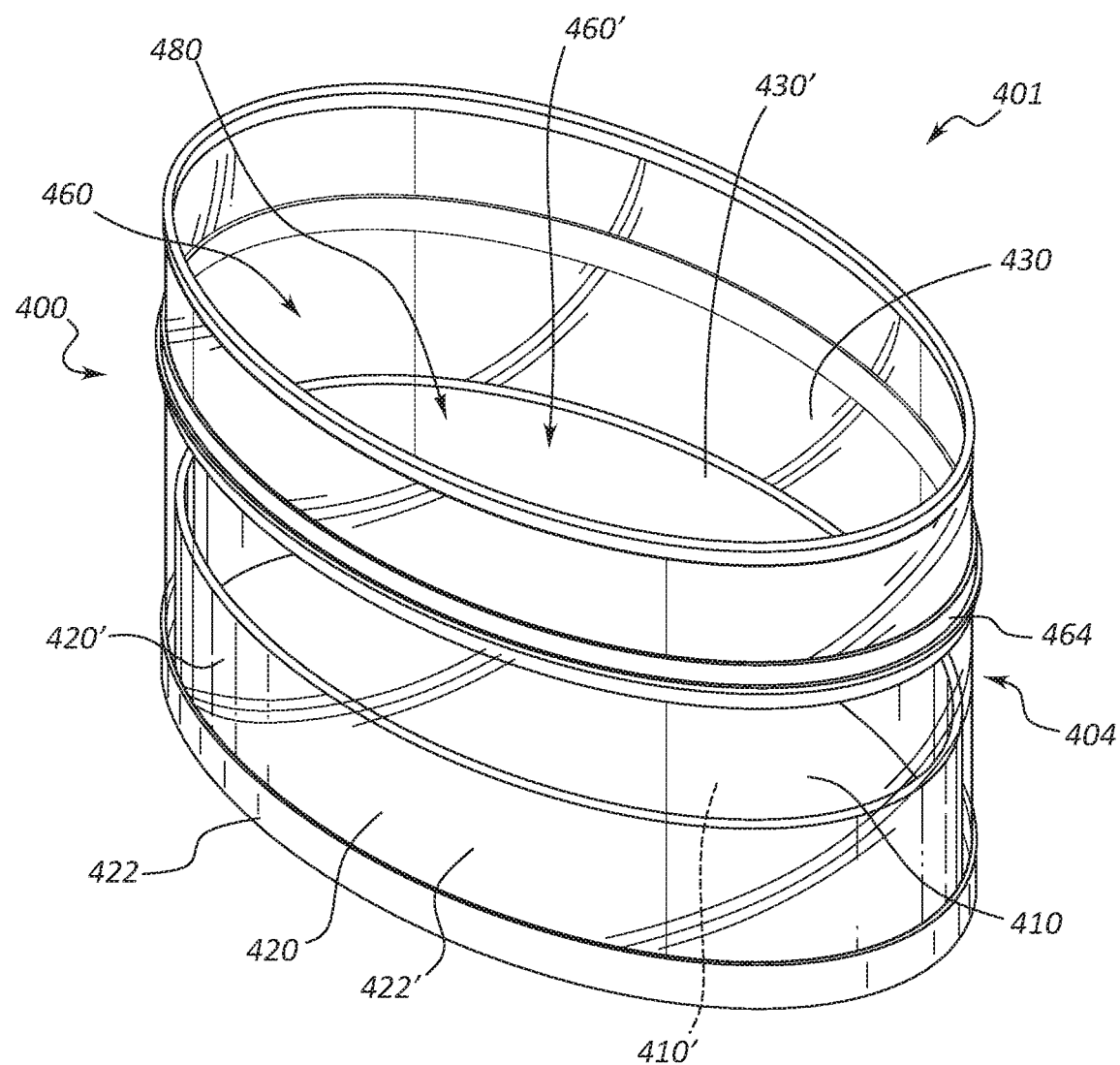
FIG. 8B is a perspective view of the medical device transport container system of FIG. 8A in an assembled configuration.

FIG. 8A is an exploded view of a medical device transport container system 401 depicting an outer container 400 and an insert portion 480. Furthermore, FIG. 8B is a perspective view of the medical device transport container system 401 wherein the insert portion 480 is disposed within and/or coupled to the outer container 400 (i.e., in an assembled configuration). In some embodiments, the insert portion 480 may be fixedly coupled to the outer container 400. For example, the insert portion 480 may be adhered to the outer container 400 (e.g., via an adhesive). In some other embodiments, the insert portion 400 may be removably coupled to the outer container 400. For example, the insert portion 480 may be disposable while the outer container 400 may be reusable. That is, the insert portion 480 may become contaminated during use of the outer container 400, and a user may discard the contaminated insert portion 480 and couple or dispose a new (e.g., uncontaminated) insert portion 480 to or within the outer container 400.

Again, as noted above, relevant disclosure set forth above regarding similarly identified features of the containers 100, 200, 300 may not be repeated in reference to the outer container 400. Likewise, relevant disclosure set forth above regarding similarly identified features of the insert portion 380 may not be repeated in reference to the insert portion 480. However, such features may clearly be the same, or substantially the same, as features depicted in other embodiments and/or described with respect to such embodiments. Accordingly, the relevant descriptions of such features apply equally to the features of the outer container 400 and insert portion 480 and related components depicted in FIGS. 8A and 8B. Furthermore, any suitable combination of the features, and variations of the same, described with respect to the containers 100, 200, 300 and the insert portion 380 and related components illustrated in FIGS. 1-7B can be employed with the medical device transport container system 401, the outer container 400, the insert portion 480, and related components of FIGS. 8A and 8B, and vice versa.

As depicted, the outer container 400 may comprise a first panel 420 disposed opposite of a second panel 430. The outer container 400 can also comprise a lower panel 410, wherein the lower panel 410 is coupled to a lower edge or lower panel edge 422, 432 of each of the first panel 420 and the second panel 430, respectively. As illustrated, each of the lower panel 410, the first panel 420, and the second panel 430 can cooperate to form a cavity 460.

The outer container 400 can further comprise a band member 464 disposed along at least a portion of a circumference of the cavity 460. The band member 464 may be coupled to a middle portion 404 of the each of the first panel 420 and the second panel 430. In certain embodiments, each of the first panel 420, the second panel 430, and the lower panel 410 may be integral. In certain other embodiments, one or more of the first panel 420, the second panel 430, and/or the lower panel 410 may be independent or separate.

As illustrated, the insert portion 480 may also comprise a first panel 420' disposed opposite of a second panel 430'. The insert portion 480 can also comprise a lower panel 410', wherein the lower panel 410' is coupled to a lower edge or lower panel edge 422', 432' of each of the first panel 420' and the second panel 430', respectively. As illustrated, each of the lower panel 410', the first panel 420', and the second panel 430' can cooperate to form a cavity 460'.

In some embodiments, one or more portions or sections of the outer container 400 may be weighted. The weighted portions of the outer container 400 may be disposed at or adjacent one or more positions wherein the lower panel 410 is coupled to the lower edges 422, 432 of each of the first panel 420 and the second panel 430, respectively. For example, one or more weights may be coupled to or disposed within at least a portion of the outer container 400 such that the outer container 400 may rest flatly on a surface. Further, the weighted portions of the outer container 400 may be formed from a heavy material and/or a material that has been folded one or more times on itself (i.e., so as to provide one or more portions of the outer container 400 with additional heft).

Likewise, one or more portions or sections of the insert portion 480 may be weighted. The weighted portions of the insert portion 480 may be disposed at or adjacent one or more positions wherein the lower panel 410' is coupled to a lower edge or lower panel edge 422', 432' of each of the first panel 420' and the second panel 430', respectively. Analogous portions or sections of the container system 401 may also be weighted, for example, such that the container system 401 may be configured to rest flatly on a surface.

In certain embodiments, each of the first panel 420', the second panel 430', and the lower panel 410' may be integral. In certain other embodiments, one or more of the first panel 420', the second panel 430', and/or the lower panel 410' may be independent or separate.

Methods related to use of medical device transport containers and medical device transport container systems are also disclosed herein. As can be appreciated, while the methods disclosed herein generally refer to medical device transport containers, each of the methods may be adapted for use with the medical device transport container systems, the outer containers, and/or the insert portions as disclosed herein.

In some embodiments, methods of using a medical device transport container may comprise disposing or placing a medical device that has become contaminated, dirty, soiled, or unsterile (i.e., during a medical procedure), within at least a portion of a cavity of the medical device transport container. The container may be used to transport medical devices including, but not limited to, endoscopes, catheters, guidewires, and so on. The contaminated medical device may then be retained or secured within at least a portion of the cavity of the medical device transport container, and the medical device transport container and the contaminated medical device retained within at least a portion of the medical device transport container may be transported from a first location to a second location. In some embodiments, the first location may be a location wherein the medical device is utilized during a medical procedure. For example, the first location may be within an operating room or a procedure room of a medical care facility such as a hospital. In some embodiments, the second location may be a location wherein the contaminated medical device is cleaned or sterilized. For example, the second location may be a cleaning facility within the medical care facility.

In some embodiments, the contaminated medical device may be positioned substantially above the medical device transport container when the medical device transport container is in an open configuration, and the contaminated medical device may be flushed with a fluid such that at least a portion of the fluid flows into the cavity of the medical device transport container. For example, a practitioner my grasp or hold the utilized medical device in a first hand and flush the utilized medical device with the fluid using a second hand. The fluid may then flush or flow over the utilized medical device, and then at least a portion of the fluid may drip or flow into an open medical device transport container that is disposed beneath, or substantially beneath, the utilized medical device. Accordingly, the medical device transport container may be liquid-tight, or substantially liquid-tight, such that upon flushing of the utilized medical device within or above the container, flow of the fluid out of the medical device transport container is limited or prevented. In some embodiments, the fluid may be selected from at least one of a cleaning solution and a sterilizing solution.

In certain embodiments, the contaminated medical device may be flushed with a fluid when the contaminated medical device is disposed within at least a portion of the cavity of the medical device transport container. As in the embodiments discussed above, the fluid may be selected from at least one of a cleaning solution and a sterilizing solution. At least a portion of the medical device transport container may be configured to absorb at least a portion of the fluid used to flush the contaminated medical device.

In some embodiments, a method of using a medical device transport container may comprise disposing a clean medical device within at least a portion of the cavity of the medical device transport container. For example, prior to utilization or contamination of the medical device, the clean or uncontaminated medical device may be disposed within the medical device transport container at a third location. The third location may be a location wherein clean medical devices are kept or stored. The method may further comprise transporting the medical device transport container and the clean medical device from the third location to the first location, and the clean medical device may be utilized during a medical procedure at the first location.

In various embodiments, the contaminated or utilized medical device may be disposed in the same medical device transport container that was used to transport the medical device prior to the contamination of the medical device. For example, the same medical device transport container that was used to transport the clean medical device from the third location to the first location may be used to transport the utilized medical device from the first location to the second location. In some embodiments, the second location may be the same as the third location.

As discussed above, in certain embodiments, the medical device may be an elongate medical device such as an endoscope. In some embodiments, a method of using the medical device transport container may further comprise disposing at least a portion of the medical device through an aperture or opening disposed in the medical device transport container such that the medical device is coupled to the medical device transport container during utilization of the medical device in a medical procedure. In some embodiments, the aperture may be disposed in a flap member coupled to the medical device transport container.

In various embodiments, the container may be configured as a stand-alone container. For example, the container may be capable of standing on its own. In certain embodiments, the container can be reused or otherwise configured for multiple uses. Additionally, the container can be a single-use container or otherwise configured for a single use. For instance, the container can be discarded after use.

In certain embodiments, the container can be foldable. For example, the container may be configured to be folded for transport and/or storage. Additionally, the container may be configured for disposition within a package such as a dispensing box. For example, a plurality of containers may be disposed within the dispensing box. In some embodiments, the dispensing box may comprise a tear-away panel and the plurality of containers disposed within the dispensing box may be dispensed through an opening of the dispensing box (e.g., an opening that is generated upon removal of the tear-away panel). The plurality of containers may be folded within the dispensing box and the containers may be configured such that they may be dispensed one at a time (e.g., for use during a medical procedure as detailed herein).

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially rectangular" is recited with respect to a feature, it is understood that in further embodiments, the feature can have a precisely rectangular configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A method of using a medical device transport container system, comprising:
   disposing a medical device that has been contaminated within at least a portion of an insert cavity of a medical device transport container system;
   securing the contaminated medical device within the medical device transport container system;
   transporting the medical device transport container system and the contaminated medical device from a first location to a second location;
   positioning the contaminated medical device substantially above the medical device transport container system when the medical device transport container system is in an open configuration;
   decontaminating the contaminated medical device with a fluid such that at least a portion of the fluid flows into the insert cavity of the medical device transport container system; and
   absorbing at least a portion of the fluid into at least a portion of the medical device transport container system.

2. The method of claim 1, wherein the fluid is selected from at least one of a cleaning solution and a sterilizing solution.

3. The method of claim 1, further comprising:
   flushing the contaminated medical device when the contaminated medical device is disposed within the insert cavity of the medical device transport container system with the fluid; and
   absorbing at least a portion of the fluid into at least a portion of the medical device transport container system.

4. The method of claim 1, wherein the medical device is contaminated during a medical procedure, the method further comprising:
   disposing the medical device, prior to the contamination of the medical device, in the medical device transport container system;
   transporting the medical device transport container system and the medical device from a third location to the first location; and
   utilizing the medical device during the medical procedure at the first location.

5. The method of claim 4, wherein the contaminated medical device is disposed in the same medical device transport container system that was used to transport the medical device prior to the contamination of the medical device.

6. The method of claim 1, further comprising:
   disposing at least a portion of the medical device through an aperture disposed in the medical device transport container system such that the medical device is coupled to the medical device transport container system during utilization of the medical device in a medical procedure.

7. The method of claim 6, wherein the aperture is disposed in a flap member coupled to the medical device transport container system.

8. The method of claim 1, wherein the medical device transport container system comprises:
   a first indicium disposed on at least a portion of an outer container, wherein the first indicium indicates to a user that at least one content of the container system is in a first state; and
   a removable label comprising a second indicium, the removable label configured to be disposed over at least a portion of the first indicium, wherein the second indicium indicates to a user that the at least one content of the container system is in a second state.

9. The method of claim 8, further comprising removing the removable label.

10. The method of claim 1, wherein the medical device transport container system comprises:
    a first indicium, wherein the first indicium indicates to a user that at least one content of the container system is in a first state; and
    a second indicium, wherein the second indicium indicates to a user that the at least one content of the container system is in a second state.

11. The method of claim 10, further comprising transitioning the medical device transport container between the first indicium and the second indicium.

12. The method of claim 1, further comprising:
    closing a closing member to transition the medical device transport container system between an open configuration and a closed configuration.

* * * * *